(12) United States Patent
March

(10) Patent No.: US 6,936,605 B2
(45) Date of Patent: Aug. 30, 2005

(54) PHARMACEUTICAL COMPOSITION

(75) Inventor: Graham Alan March, Surrey (GB)

(73) Assignee: Special Products Limited, Addlestone (GB)

( * ) Notice: Subject to any disclaimer, the term of this patent is extended or adjusted under 35 U.S.C. 154(b) by 404 days.

(21) Appl. No.: 10/317,518

(22) Filed: Dec. 12, 2002

(65) Prior Publication Data

US 2003/0130267 A1 Jul. 10, 2003

(30) Foreign Application Priority Data

Dec. 24, 2001 (GB) .............................................. 0130964

(51) Int. Cl.$^7$ ......................... A61K 31/55; A61K 31/70
(52) U.S. Cl. ........................ 514/220; 514/772; 514/785; 514/816; 514/25
(58) Field of Search ................................ 514/220, 772, 514/785, 816, 25

(56) References Cited

U.S. PATENT DOCUMENTS 4,777,065 A * 10/1988 Hirao et al. ................. 427/239

FOREIGN PATENT DOCUMENTS

| WO | WO 99/09989 A1 | 3/1999 |
| WO | WO 00/62764 A1 | 10/2000 |
| WO | WO 01/30391 A2 | 5/2001 |

OTHER PUBLICATIONS

Caplus DN 127:336674, Kondo T, JP 09278671, 19971028, abstract.*

Micromedex, Inc., online Drug Information for Midazolam, revised Jan. 13, 2002, pp. 1–3.*

James Fish, "Midazolam" University of Michigan Department of Anesthesiology Web Project, University of Michigan Medical School, Ann Arbor, Michigan, USA (Apr. 15, 1997) pp. 1–3.

Eli Lahat et al. "Comparison of Intransal Midazolam with Intravenous Diazepam for Treating Febrile Seizures in Children: Prospective Randomised Study" BMJ, vol. 2000, No. 321 (Jul. 8, 2000) pp. 83–86.

Roche "Versed (midazolam HCl) Syrup"product information from printed from the Roche Laboratories websites at www.rocheusa.com/products/versed/pi_syr.html (Dec. 1998) pp. 1–19.

Rod C. Scott et al. "Buccal Midazolam and Rectal Diazepam for Treatment of Prolonged Seizures in Childhood and Adolescence: A Randomised Trial" The Lancet, vol. 353 (Feb. 20, 1999) pp. 623–626.

Roelofse et al.; Intranasal Midazolam Spray in Adults; Rsearch Article; Jun. 2000, SAJAA.

* cited by examiner

*Primary Examiner*—Rebecca Cook

(57) ABSTRACT

A liquid pharmaceutical composition is described comprising from about 7.5 mg/mL to about 12.5 mg/mL of midazolam in the form of midazolam maleate in solution in an aqueous liquid medium comprising ethanol and a polyhydroxy solvent. This composition can be administered by the buccal route for the treatment of patients suffering epileptic siezures or as an anaesthetic.

16 Claims, No Drawings

PHARMACEUTICAL COMPOSITION

This invention relates to a pharmaceutical composition. In particular it relates to a liquid pharmaceutical composition suitable for buccal administration for the treatment of epilepsy. It further relates to a liquid pharmaceutical composition suitable for buccal administration as an anaesthetic.

BACKGROUND OF THE INVENTION

Midazolam, i.e. 8-chloro-6-(2-fluorophenyl)-1-methyl-4H-imidazo[1,5-a][1,4]diazepine of the formula:

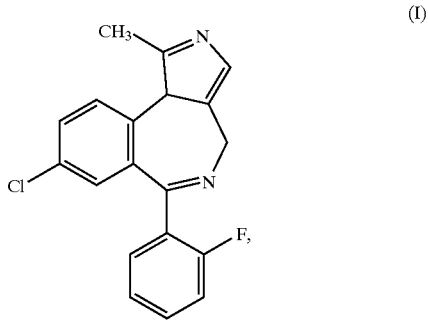

is a well-documented product with sedative, anxiolytic, amnesic and hypnotic properties. It is commercially available in the form of its hydrochloride, for example in the form of a glycerin-based syrup sold under the trade mark VERSED® which contains 2.5 mg/mL of midazolam. It is also sold in the form of its maleate salt, for example in tablets containing 7.5 mg or 15 mg per tablet of midazolam under the trade mark DORMICUM®. The maleate salt contains 1:1 midazolam:maleic acid on a molar basis and hence is an acid salt.

It is known that midazolam can exist in solution both in a closed ring form and also in an open ring form which are in equilibrium with one another:

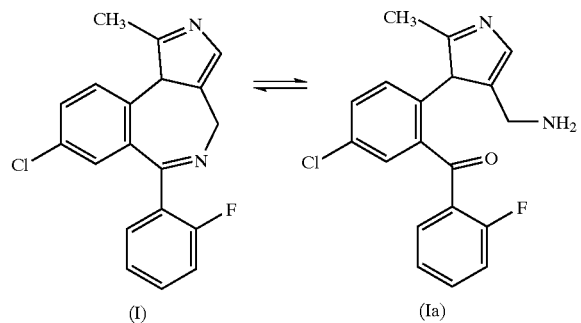

The amount of the open ring form (Ia) present in aqueous solution depends upon the pH of the solution. In a typical syrup for oral administration, i.e. VERSED® syrup, the pH is typically approximately 3 and the proportion of the open ring form (Ia) may be about 40%. However, at physiological pHs of about 7.4, any open ring form present is reported to revert to the physiological, lipophilic closed ring form (I) and is absorbed as such.

Epileptic seizures (convulsive status epilepticus) are a common cause of neurological medical emergency and often result in brain damage. Failure to relieve the symptoms of an epileptic seizure in less than about 15 minutes can lead to death. Accordingly it is extremely desirable to treat very promptly a patient with an epileptic seizure and to relieve the corresponding symptoms as quickly as possible so as to minimise the risk of brain damage or death for the patient.

A comparison between intranasal and intravenous administration of midazolam for treating epileptic seizures in children has been described by E. Lahat et al., BMJ 2000: 321: pages 83 to 86 (8Jul. 2000). A dosage of 0.2 mg/kg intranasal midazolam is recommended with the corresponding recommended intravenous dose corresponding to 0.3 mg/kg. A solution containing 5 mg/mL of midazolam was used for intranasal administration. Control of seizures in used for intranasal administration. Control of seizures in children was reported to be faster by the intravenous route but the time to cessation of seizures was faster using the intranasal route.

Buccal administration of midazolam to treat seizures in students suffering from epilepsy has been reported by R. C. Scott et al., The Lancet, 353, Feb. 20, 1999, pages 623 to 626. These studies were conducted using a solution containing midazolam hydrochloride. The dosage used was 2 mL (10 mg) which was drawn into a 2 mL syringe. For administration the patient's lips were parted and the contents of the syringe squirted around buccal mucosa. However, even when the amount of liquid to be administered is no more than 2 mL, there may be difficulty in actually administering this quantity to a patient suffering an epileptic seizure whose jaws are clamped tightly shut as a result of the seizure.

Another well known use of midazolam is as an anaesthetic. Typically midazolam is administered intramuscularly when used as an anaesthetic. However, in emergency situations, such as at the scene of a car crash, particularly when the patient is wearing bulky clothing and has suffered bone fracture, the use of the intramuscular route may not be desirable.

There is accordingly a need to provide an improved form of medicament for the treatment of patients suffering epileptic seizure. There is a further need to provide a novel form of liquid pharmaceutical composition which enables an effective dose of midazolam (e.g. about 10 mg) to be administered quickly and without difficulty to a patient suffering from an epileptic seizure. It would further be desirable to provide a form of medicament for administration via the buccal route in which a higher proportion of midazolam is present in the closed ring form (I) so as to be more readily fat-soluble and thus better able to cross the blood-brain barrier faster than forms of midazolam which contain a high proportion of the open ring form (Ia). In addition there is a need to provide a liquid medicament suitable for buccal administration as an effective anaesthetic for use in accident and other emergency situations to relieve pain until the patient can be transferred to hospital.

SUMMARY OF THE INVENTION

The present invention accordingly seeks to provide a liquid pharmaceutical preparation containing midazolam which contains a higher concentration of midazolam than prior art liquid preparations containing midazolam. It further seeks to provide a liquid medicament which contains a higher proportion of the closed ring form of midazolam (I) than liquid midazolam-containing formulations of the prior art. Yet again it seeks to provide an improved form of liquid medicament which can be used for buccal administration for the treatment of patients suffering epileptic seizures. In addition, it seeks to provide an improved form of liquid midazolam-containing composition which contains a high concentration of midazolam and is suitable for administration by the buccal route as an anaesthetic. Another objective is to provide a novel method of administering midazolam to a patient requiring treatment therewith, for example a patient suffering from an epileptic seizure or requiring anaesthetisation.

DESCRIPTION OF THE PREFERRED EMBODIMENT

The invention envisages the use of midazolam maleate for the preparation of a liquid medicament for administration by the buccal route. In a preferred aspect the invention envisages the use of such a medicament for the treatment of patients suffering epileptic seizures. In another of its preferred aspects the invention envisages the use of the medicament as an anaesthetic. Typically such a medicament contains from about 7.5 mg/mL to about 12.5 mg/mL of midazolam.

The invention further provides a liquid pharmaceutical composition comprising from about 7.5 mg/mL to about 12.5 mg/mL of midazolam in the form of midazolam maleate in solution in an aqueous liquid medium comprising ethanol and a polyhydroxy solvent, such as glycerol or propylene glycol.

It is further preferred that the pH of the composition lies in the range of from about 4.5 to about 5.5.

It is desirable that the composition further comprises a sweetening agent. The sweetening agent is preferably a synthetic sweetening agent such as an alkali metal salt of saccharin, e.g. sodium saccharin, potassium acesulfame or cyclamate. The amount of sweetening agent preferably ranges from about 1 g up to about 10 g per 100 ml of the composition.

The composition may further comprise a viscosity adjustment agent, such as a hydrogenated starch hydrolysate. Such a viscosity adjustment agent is desirably added to the composition in an amount sufficient to impart to the composition a viscosity high enough to permit the composition to be drawn into an oral syringe and for at least a major part of a unit dosage administered to be retained in the patient's mouth without a significant amount trickling down into the patient's oesophagus or windpipe. A suitable hydrogenated starch hydrolysate is, for example a maltitol syrup. A typical maltitol syrup is that sold under the trade Lycasin® 80/55 by Roquette Frères, 62080 Lestrem, France. The amount of viscosity adjustment agent is preferably sufficient to impart to the composition a viscosity of from about 270 CP (about 0.27 Pa.sec) to about 330 CP (about 0.33 Pa.sec) measured at 22° C.

The composition may also contain an antifungal agent. Typical antifungal agents include alkali metal salts of an alkyl hydroxybenzoate, such as sodium methyl hydroxybenzoate, sodium propyl hydroxybenzoate, or a mixture thereof. The amount of antifungal agent may range for example, from about 0.05 g of up to about 1.00 g per 100 ml of the composition, preferably from about 0.10 g up to about 0.50 g per 100 ml of the composition.

An especially preferred composition comprises per 100 mL of the composition:

from about 1.0 to about 1.5 g of midazolam maleate;

from about 1.0 to about 5.0 g of an alkali metal salt of saccharin;

from about 5.0 to about 8.0 mL of purified water;

from about 0.1 to about 0.4 g of an alkali metal salt of methyl hydroxybenzoate;

from about 0.025 g to about 0.075 g of an alkali metal salt of propyl hydroxybenzoate;

from about 17.5 to about 25 mL of ethanol;

from about 5.0 to about 10.0 mL of glycerol;

sufficient sodium hydroxide to bring the pH to from about 4.5 to about 5.5; and the balance comprising a solution of a hydrogenated starch hydrolysate.

The liquid pharmaceutical composition of the invention is suitable for buccal administration for treatment of epileptic seizures or for buccal administration as an anaesthetic. Typically a unit dosage form of the composition, which is preferably about 1 mL, contains about 10 mg midazolam.

The invention is further illustrated in the following Examples.

EXAMPLE 1

The following ingredients were used to prepare a liquid pharmaceutical composition:

| | |
|---|---|
| Midazolam maleate | 1.360 g |
| Sodium saccharin | 4.000 g |
| Purified water | 6.000 mL |
| Sodium methyl hydroxybenzoate | 0.200 g |
| Sodium propyl hydroxybenzoate | 0.050 g |
| Ethanol (96%) | 20.000 mL |
| Glycerol | 7.500 mL |
| Sodium hydroxide to pH 4.5 to 5.5 | q.s. |
| Lycasin ® 80/55 to | 100.000 mL |

To prepare the liquid pharmaceutical composition, 7.5 mL of glycerol were added to 20.0 mL 96% ethanol and mixed. 1.36 g of midazolam maleate was dissolved in the resulting glycerol/ethanol solution. The resulting midazolam maleate solution was then added to 60.0 mL of Lycasin® 80/55 and mixed. In a separate vessel 4.00 g of sodium saccharin, 0.20 g of sodium methyl hydroxybenzoate and 0.05 g of sodium propyl hydroxybenzoate were dissolved in 6.0 mL of purified water. The resulting aqueous solution was added to the midazolam-containing preparation. Mixing is continued until no particles are visible. Then the pH is adjusted to a value within the range of from about 4.5 to about 5.5, whereafter the resulting solution is made up to 100.0 mL by addition of more Lycasin® 80/55.

Lycasin® 80/55 is a hydrogenated starch hydrolysate, more specifically a 55% maltitol syrup, sold by Roquette Frères, 62080 Lestrem, France.

EXAMPLE 2

A larger batch was made using the same general method as in Example 1 using the following ingredients:

| | |
|---|---|
| Midazolam maleate | 68.0 g |
| Sodium saccharin | 200.0 g |
| Purified water | 300.0 mL |
| Sodium methyl hydroxybenzoate | 20.0 g |
| Sodium propyl hydroxybenzoate | 2.5 g |
| Ethanol (96%) | 1000.0 mL |
| Glycerol | 375.0 mL |
| Sodium hydroxide to pH 4.5 to 5.5 | q.s. |
| Lycasin ® 80/55 to | 5000.0 mL |

EXAMPLE 3

5 mL of the product of Example 1 or Example 2 was placed in a labelled 30 mL amber glass bottle with a white bottle adaptor and a child-resistant screw cap and placed in a labelled cardboard carton. The carton also contained 4×1 mL oral syringes. The instructions for use were printed on the carton.

The product was tested successfully for buccal administration for the treatment of epileptic seizures and also as an anaesthetic, in a dosage of 1 mL applied using an oral syringe.

By filling the bottle with only 5 mL of the liquid product the risk of accidental administration of a fatal or dangerous overdose is substantially minimised.

I claim:

1. A liquid pharmaceutical composition suitable for buccal administration comprising from about 7.5 mg/mL to about 12.5 mg/mL of midazolam in the form of midazolam maleate in solution in an aqueous liquid medium comprising ethanol and a polyhydroxy solvent, the composition having a pH in the range of from about 4.5 to about 5.5 and further comprising a viscosity adjustment agent in an amount sufficient to impart to the composition a viscosity of from about 270 CP (about 0.27 Pa.sec) to about 330 CP (about 0.33 Pa.sec) measured at 22° C. wherein the viscosity adjustment agent comprises a maltitol syrup.

2. The liquid pharmaceutical composition according to claim 1, wherein the polyhydroxy solvent comprises glycerol.

3. The liquid pharmaceutical composition according to claim 1, further comprising a sweetening agent.

4. The liquid pharmaceutical composition according to claim 3, wherein the sweetening agent comprises an alkali metal salt of saccharin.

5. The liquid pharmaceutical composition according to claim 4, wherein the alkali metal salt of saccharin comprises sodium saccharin.

6. The liquid pharmaceutical composition according to claim 1, further comprising an antifungal agent.

7. The liquid pharmaceutical composition according to claim 6, wherein the antifungal agent comprises an alkali metal salt of an alkyl hydroxybenzoate.

8. The liquid pharmaceutical composition according to claim 7, wherein the alkali metal salt of an alkyl hydroxybenzoate is selected from sodium methyl hydroxybenzoate, sodium propyl hydroxybenzoate, and mixtures thereof.

9. The liquid pharmaceutical composition according to claim 1, which comprises per 100 mL of the composition:

from about 1.0 to about 1.5 g of midazolam maleate;

from about 1.0 to about 5.0 g of an alkali metal salt of saccharin;

from about 5.0 to about 8.0 mL of purified water;

from about 0.1 to about 0.4 g of an alkali metal salt of methyl hydroxybenzoate;

from about 0.025 g to about 0.075 g of an alkali metal salt of propyl hydroxybenzoate;

from about 17.5 to about 25 mL of ethanol;

from about 5.0 to about 10.0 mL of glycerol;

sufficient sodium hydroxide to bring the pH to from about 4.5 to about 5.5; and the balance comprising a solution of a hydrogenated starch hydrolysate.

10. The liquid pharmaceutical composition according to claim 1, suitable for buccal administration for treatment of epileptic seizures.

11. The liquid pharmaceutical composition according to claim 1, suitable for buccal administration as a general anaesthetic.

12. The liquid pharmaceutical composition according to claim 1, in unit dosage form containing about 10 mg midazolam.

13. The liquid pharmaceutical composition according to claim 12, in which a unit dosage form comprises about 1 mL.

14. A method of administering midazolam to a patient requiring treatment therewith which comprises administering to the patient by the buccal route an effective amount of midazolam in the form of a liquid pharmaceutical composition according to claim 1.

15. A method of treatment of an epileptic seizure in a patient comprising administering to said patient by the buccal route an effective amount of midazolam in the form of a liquid pharmaceutical composition containing midazolam maleate according to claim 1.

16. A method of inducing general anaesthesia in a patient which comprises administering to the patient by the buccal route an effective amount of midazolam in the form of a liquid preparation containing midazolam maleate according to claim 1.

* * * * *